(12) United States Patent
Schwarz (10) Patent No.: US 11,083,362 B2
(45) Date of Patent: Aug. 10, 2021

(54) MEDICAL DEVICE FOR MOVING A MEDICAL INSTRUMENT

(71) Applicant: UROMED Kurt Drews KG, Oststeinbek (DE)

(72) Inventor: Werner Schwarz, Ruhpolding (DE)

(73) Assignee: UROMED Kurt Drews KG, Oststeinbek (DE)

( * ) Notice: Subject to any disclaimer, the term of this patent is extended or adjusted under 35 U.S.C. 154(b) by 0 days.

(21) Appl. No.: 16/763,471

(22) PCT Filed: Nov. 14, 2018

(86) PCT No.: PCT/EP2018/081207
§ 371 (c)(1),
(2) Date: May 12, 2020

(87) PCT Pub. No.: WO2019/096835
PCT Pub. Date: May 23, 2019

(65) Prior Publication Data
US 2020/0359878 A1 Nov. 19, 2020

(30) Foreign Application Priority Data
Nov. 14, 2017 (DE) .................... 10 2017 010 535.9

(51) Int. Cl.
*A61B 1/00* (2006.01)
*A61B 17/221* (2006.01)
(Continued)

(52) U.S. Cl.
CPC ...... *A61B 1/00158* (2013.01); *A61B 1/00066* (2013.01); *A61B 1/00085* (2013.01);
(Continued)

(58) Field of Classification Search
CPC ........ A61F 2/95; A61F 2/9517; A61F 2/9522; A61F 2002/9505; A61F 2002/9511;
(Continued)

(56) References Cited

U.S. PATENT DOCUMENTS 5,364,352 A * 11/1994 Cimino ................ A61B 5/6855
604/95.04
5,496,330 A 3/1996 Bates et al.
(Continued)

FOREIGN PATENT DOCUMENTS

CN 103826555 A 5/2014
CN 104955620 A 9/2015
(Continued)

OTHER PUBLICATIONS

International Search Report dated Jan. 31, 2019 filed in PCT/EP2018/081207.
(Continued)

*Primary Examiner* — Wade Miles
*Assistant Examiner* — Kankindi Rwego
(74) *Attorney, Agent, or Firm* — Rankin, Hill & Clark LLP (57) ABSTRACT

The aim of the invention is to move a medical instrument (2) by means of a medical device (1) in the longitudinal direction of the device and in the rotation direction transversely about the longitudinal direction by an actuating apparatus (3). This aim is achieved in that the medical instrument (2) is connected to at least one first magnetic element (18, 19) and the actuating apparatus (3) contains at least one second magnetic element (20, 21) or is connected thereto; the actuating apparatus (3) is movable together with the at least one second magnetic element (20, 21) in the longitudinal direction of the device and in the rotational direction about the longitudinal direction in question and is movable (Continued)

together with the at least one second magnetic element (20, 21) in the longitudinal direction of the device and in the rotational direction about the longitudinal direction in question and permits, by means of magnetic coupling between the at least one second magnetic element (20, 21) and the at least one first magnetic element (18, 19), moving same together with the medical instrument (2).

11 Claims, 9 Drawing Sheets

(51) Int. Cl.
 *A61B 17/00* (2006.01)
 *A61B 1/307* (2006.01)
(52) U.S. Cl.
 CPC ............ *A61B 1/307* (2013.01); *A61B 17/221* (2013.01); *A61B 2017/00876* (2013.01); *A61B 2017/2212* (2013.01)
(58) Field of Classification Search
 CPC .............. A61M 25/01; A61M 25/0127; A61M 25/0133; A61M 25/0136; A61M 25/0158; A61M 25/09; A61M 2025/09116; A61M 2025/09125; A61B 17/2841; A61B 17/2909; A61B 1/00066; A61B 1/00085; A61B 1/00158; A61B 1/307; A61B 2017/00876; A61B 17/221; A61B 17/32056; A61B 2017/2212; A61B 2017/2215; A61B 2017/2217
 USPC ... 606/106, 1, 108, 110, 113, 114, 127, 128; 600/104, 105, 106
 See application file for complete search history.

(56) References Cited

U.S. PATENT DOCUMENTS

| | | | |
|---|---|---|---|
| 5,545,200 A * | 8/1996 | West | A61B 18/1492 606/29 |
| 6,391,027 B1 * | 5/2002 | Farin | A61B 18/042 606/34 |
| 2003/0009176 A1 | 1/2003 | Bilitz | |
| 2004/0087848 A1 | 5/2004 | Mejia | |
| 2009/0125024 A1 | 5/2009 | Baur | |
| 2010/0030031 A1 * | 2/2010 | Goldfarb | A61B 1/00183 600/163 |
| 2010/0191224 A1 * | 7/2010 | Butcher | A61B 34/76 606/1 |
| 2013/0085498 A1 | 4/2013 | Matusaitis et al. | |
| 2013/0317534 A1 | 11/2013 | Zhou et al. | |
| 2016/0030121 A1 | 2/2016 | Inoue | |
| 2016/0158041 A1 * | 6/2016 | Roeder | A61F 2/86 623/1.11 |
| 2016/0199079 A1 | 7/2016 | Chu et al. | |
| 2019/0175873 A1 | 6/2019 | Uihlein | |

FOREIGN PATENT DOCUMENTS

| | | |
|---|---|---|
| CN | 107106193 A | 8/2017 |
| DE | 69433774 T2 | 4/2005 |
| JP | 2004160219 A | 6/2004 |
| JP | 2009500092 A | 1/2009 |
| JP | 2015517392 A | 6/2015 |
| WO | 2017153178 A1 | 9/2017 |

OTHER PUBLICATIONS

Olympus No-Tip Nitinol Stone Retrieval Baskets, https://www.youtube.com/watch?v=2BhfMzx5pNE dated Oct. 13, 2014; cited in Specification.

Chinese Search Report dated Oct. 21, 2020 for the corresponding Chinese Patent Application No. 201880071945.9; machine translation.

Japanese Office Action dated Oct. 2, 2020 for the corresponding Japanese Patent Application No. 2020-544153; machine translation.

* cited by examiner

Section I-I

FIG. 7

Section I-I

Enlarged cut-out of Fig. 11

FIG. 13

Enlarged cut-out of Fig. 11

FIG. 14

Enlarged cut-out of Fig. 11

FIG. 15

Enlarged cut-out of Fig. 11

MEDICAL DEVICE FOR MOVING A MEDICAL INSTRUMENT

BACKGROUND

The invention relates to a medical device, preferably a device for use in a medical endoscope, for moving a medical instrument, preferably a stone retrieval instrument, in the device longitudinal direction and in the direction of rotation that is transverse about the particular longitudinal direction, by means of an actuating means.

A medical device of the above-mentioned type is already known (see: https://www.youtube.com/watch?v=2BhfMzx5pNE on the Internet). This known device needs two hands to operate it or to be grasped: a first hand is used to extend or insert a stone retrieval basket out of or into the device, and a second hand is used to open or close the stone retrieval basket. Occasionally, however, operation of the device of this type is perceived to be too complex.

Therefore, the object of the invention is to form a medical device of the type mentioned at the outset such that the medical instrument can be moved in a relatively simple manner by means of an actuating means in both the device longitudinal direction and the direction of rotation that is transverse about the particular longitudinal direction by single-handed operation.

DESCRIPTION

According to the invention, the object demonstrated above is achieved in a medical device of the type mentioned at the outset in that the medical instrument contains at least one first magnetic element or is connected thereto, the actuating means contains at least one second magnetic element or is connected thereto, and the actuating means, together with the at least one second magnetic element, is either mechanically coupled and the at least one first magnetic element is only able to move in said direction of rotation as a result of magnetic coupling, or without mechanical coupling, the at least one first magnetic element is able to move both in said device longitudinal direction and in the particular direction of rotation as a result of magnetic coupling.

In this case, the "medical device" is preferably a device for use in a medical endoscope, which can be used to remove kidney stones, stones in the urethra or other concretions, for example. In order to pass passage instruments through, the medical device comprises an elongate outer tube.

The "medical instrument" is a passage instrument that can be received in the outer tube of the medical device or passes therethrough, i.e. that is arranged inside the outer tube of the medical device, preferably a stone retrieval instrument. The medical instrument is mounted in the medical device, in particular in the outer tube, such that it can move axially (longitudinally) and can rotate about its longitudinal axis. The axial movement and rotation about the longitudinal axis of the instrument are brought about by means of the actuating means described herein.

The invention is advantageous in that the medical instrument can be moved by means of an actuating means in a relatively simple manner by single-handed operation both in the device longitudinal direction and in the direction of rotation that is transverse about the particular longitudinal direction.

The use according to the invention of two magnetically coupled elements has the particular additional advantage that the interacting magnetic elements also act as safety means that prevent the distal operating element from being destroyed by the user applying too great a force. Therefore, in commercially available instruments, the operating element (for example the stone retrieval basket) can get damaged if the user after catching the concretion retracts the operating element into the outer tube in the proximal direction under too great an application of force. If the first and second magnetic elements, which interact as per the invention, are used, in such a case when excessive force is applied, the magnetic interaction of the elements is interrupted and the actuating element is moved further in the proximal direction, thereby breaking the magnetic interaction.

If the at least one second magnetic element and the at least one first magnetic element are mechanically coupled to one another in said device longitudinal direction, the at least one first magnetic element can only move in said direction of rotation as a result of magnetic coupling. Without such a mechanical coupling, the at least one first magnetic element can, however, move both in said device longitudinal direction and in the particular direction of rotation as a result of magnetic coupling.

According to an expedient development of the invention, a scale means or a scale element is preferably assigned to the actuating means, which is permitted to indicate or establish the size of at least one movement of the medical instrument in the device longitudinal direction and/or in the direction of rotation that is transverse thereto. It may be advantageous to establish the size of the movement of the medical instrument both in the device longitudinal direction and in the direction of rotation that is transverse thereto, i.e. by means of two scales and to therefore establish this size in two coordinates. This is useful in particular when the particular medical instrument is to be used to extract body parts of concretions, for example gallstones or kidney stones, from cavities in an individual. In this case, before such extraction, it is advantageous to at least have some rough information about how big the body part to be removed or the particular concretion is. This means that said scale means or said scale element can, to some extent, be used to measure the body parts to be removed or the particular concretion in each case.

According to another expedient development of the invention, the present medical device comprises the following features:

the medical device comprises a proximal end or end region that allows for, or at least facilitates, handling thereof and a distal end or end region that contains the medical instrument, the medical instrument comprises an operating end that protrudes from the distal end of the device or can be extended therefrom and can be moved by an instrument receiving body in both the device longitudinal direction and in the direction of rotation that is transverse thereto by means of its region that connects to this operating end towards the proximal end of the device, in the instrument receiving body, the at least one first magnetic element is coupled to the medical instrument, and the at least one first magnetic element is surrounded by the at least one second magnetic element, which can move in relation to the at least one first magnetic element in the device longitudinal direction and in the direction of rotation that is transverse thereto and which interacts with the at least one first magnetic element.

The advantage of this is a medical device according to the invention that is, as a whole, particularly simple to form.

Expediently, the at least one second magnetic element is received by a rotary slide, which, together with the at least one second magnetic element, can move around the at least one first magnetic element in both the device longitudinal direction and in the direction of rotation that is transverse thereto. As a result, the at least one second magnetic element can advantageously move in a particularly simple manner relative to the at least one first magnetic element in both the device longitudinal direction and in the direction of rotation that is transverse thereto.

The rotary slide is preferably movable and rotatable between the receiving body and an extension part, which is provided proximally in the device longitudinal direction, can be used as a hand-supporting body and can be received by the receiving body. This measure makes it easier to operate the medical device according to the invention with one hand.

The at least one first magnetic element and the at least one second magnetic element are expediently arranged such that they interact with opposite magnetic poles. This gives the advantage of a particular simple design of the at least one first and second magnetic elements.

Expediently, the magnetic elements are formed by bar magnets, the opposite poles of which (north and south poles) are each oriented in the device longitudinal direction. Alternatively thereto, the particular magnetic elements can be formed by circular magnets, the opposite poles of which (north and south poles) are each oriented transversely to the device longitudinal direction. In both cases, magnetic elements that are easy to construct are therefore provided.

The particular magnetic elements are preferably formed by permanent magnets. The advantage of this is magnetic elements that are particularly simple to implement. However, it should be noted at this point that in principle it is also possible for one of the magnetic elements or the other magnetic element or all of the magnetic elements to each be formed by an electromagnetic element.

An endoscopically usable medical instrument, a medical stone retrieval basket or a medical snare, such as a polypectomy snare, can preferably be used as the medical instrument.

Therefore, the present invention can be applied to another field of medicine, such as in the gall and renal regions and in gastroenterology.

The medical instrument preferably comprises a shaft part, which is flexible or flexurally elastic. The flexibility of the shaft part makes it possible to insert the instrument through the outer tube of a medical device and to push it through this tube up to the surgical site. The device used in combination with the instrument preferably likewise comprises a flexible shaft part, which can be formed by the outer tube or comprises an outer tube.

The proximal end or end region of the medical device that allows for, or at least facilitates, handling thereof can be a handle or comprise a handle. The handle can comprise an end gripping part, for example. The handle is preferably designed to be operated single-handedly. This means that all functions implemented in the handle, including holding the device and actuating the actuating element described here, can be operated with one hand.

In preferred embodiments, a scale element is assigned to the actuating means, which can indicate the length or size of a concretion caught in the stone retrieval basket. For this purpose, a scale arranged on the scale element is pushed forwards by magnetic force in the distal direction between the rotary slide and the cover tube in a positively guided manner if the rotary slide is moved as far as possible in the proximal direction. This effect is achieved by the use of a scale element having an L-shaped cross section, which is preloaded by a spring in the actuating means and pushed as far as possible in the proximal direction, wherein the scale is not visible to the user in this position, since it is arranged between the rotary slide and the cover tube. The second magnetic element is arranged proximally to the scale element. If a concretion is received in the stone retrieval basket and if the rotary slide is moved as far as possible in the proximal direction by the user, the magnetic force of the first magnetic element holds the second magnetic element in a position that is distal from its maximum proximal position. Accordingly, the spring element used to create preload is compressed and the scale between the rotary slide and the cover tube is pushed forwards in the distal direction so that the scale is visible to the user. Therefore, according to the invention, a scale element can be moved in the distal direction by means of a longitudinal movement of the at least one second magnetic element in the distal direction.

For this purpose, the scale element comprises a first part, which comprises a scale and which is arranged in parallel with the longitudinal direction of the medical instrument or in parallel with the shaft region thereof. The first part can, for example, rest against the cover tube of the medical device and have a complementary shape thereto, at least in portions.

Therefore, the first part can have a partially circular cross section, for example, which matches the cylindrical shape of the cover tube. At least portions of the first part of the scale element are arranged between the cover tube and the actuating means or the rotary slide of the actuating means. A second part of the scale element is arranged at the proximal end of the first part.

The second part of the scale element is arranged substantially orthogonally to the longitudinal direction of the first part and therefore also substantially orthogonally to the longitudinal direction of the medical instrument. The scale element can, for example, be formed from a substantially L-shaped element, for example a sheet metal, plastics or ceramic element. The short end of the L shape would form the second part of the scale element and the long end the first part in this case. In this context, "L shape" denotes a shape having an L-shaped cross section. The scale element is preferably formed of one piece. In any case, however, the first and the second part of the scale element cannot move relative to one another.

The second part of the scale element is arranged entirely between the rotary slide and the cover tube. A spring element is arranged distally from the second part—and preferably radially next to a portion of the first part. The spring element exerts a preload from the distal direction on the second part. The second magnetic element is arranged proximally to the second part. In other words, the second part of the scale element is therefore arranged between the spring element and the second magnetic element. By means of a longitudinal movement of the at least one second magnetic element in the distal direction, the scale element can therefore move in the distal direction. Therefore, a part of the scale element that is spring-preloaded in the proximal direction is arranged distally from the at least one second magnetic element in the cavity.

The spring element, the second magnetic element (or a magnetic component thereof) and the second part of the scale element are preferably arranged in a cavity in the rotary slide or actuating element. The second magnetic element and the second part of the scale element can move longitudinally inside the cavity, in parallel with the longitudinal axis of the medical device. By means of this longitudinal movement, the spring element can be compressed. In other words, the actuating means therefore comprises at least one cavity, in which the at least one second magnetic element is arranged such it can move longitudinally.

In a non-operative state in which a concretion is not received in the stone retrieval basket and the stone retrieval basket can therefore be fully retracted into the outer tube, the second part and the second magnetic element (or the magnetic component thereof) are moved into the proximal end region, preferably at the proximal end of the cavity, by means of the spring force exerted by the spring element in the proximal direction. If, conversely, a concretion is received in the stone retrieval basket and if the rotary slide is moved into its most proximal position, the second magnetic element (or the magnetic component thereof) is moved inside the cavity to a more distal position by means of the magnetic interaction with the first magnetic element—which can no longer be drawn back into its most proximal position as a result of its coupling to the pulling and sliding strand.

In a related aspect, the invention relates to a medical device, preferably to the use thereof in a medical endoscope, preferably a device comprising magnetic coupling of the type described here, for moving a medical instrument in the device longitudinal direction and in the direction of rotation that is transverse about the particular longitudinal direction by means of an actuating means, characterized in that the device comprises a gripping part that comprises an opening at its proximal end, into which an insertion aid can be inserted and in which the insertion aid can be clampingly locked.

The invention also relates to a medical system, which comprises a medical device as per the invention and an insertion aid, wherein the insertion aid is preferably locked in the proximal opening of the gripping part of the medical device.

Before the medical instrument is inserted into the operating channel of an endoscope, the insertion aid can be inserted or pushed into the proximal inlet connecting piece of the operating channel. It can therefore be removed via the opening in the device. The insertion aid is funnel-like and facilitates the insertion of the distal end of the medical instrument into the inlet connecting piece. The reversible locking of the insertion aid to the proximal end of the gripping part is advantageous in that the sterile outer packaging of the medical device only has to be opened slightly at the proximal end in order to obtain access to the insertion aid. In order to attach the insertion aid to the inlet connecting piece, the medical device can firstly be put to the side, without the risk of the distal end region of the device or instrument becoming unsterile. Subsequently, the distal end region can likewise be removed from the sterile outer packaging and swiftly inserted into the operating channel.

The insertion aid is generally cylindrical in its proximal end region for this purpose. The distal end region of the insertion aid comprises a portion that converges in the distal direction in the shape of a funnel (conically). Distally adjoining the conical portion, the insertion element can comprise an additional cylindrical portion. This portion has a smaller outer circumference than the proximal end region of the insertion aid. Suitable insertion aids are known to persons skilled in the art.

In order to reversibly lock it in the proximal opening of the handle, the insertion aid can comprise bulge-like ribs, each of which extend along a circumference of the insertion aid, preferably along a circumference in the proximal end region. In these embodiments, the handle accordingly comprises clamping elements on the proximal opening, by means of which the insertion aid can be locked. The clamping elements usually preferably engage between the ribs and slide over the ribs when the insertion aid is inserted and removed via the opening. It goes without saying that the shape of the opening is preferably complementary to the cross section of the insertion aid, at least in part. The opening is preferably substantially circular or partially circular, whereby the internal diameter of the circle corresponds to the external diameter of the insertion aid. The opening is preferably arranged transversely to the longitudinal direction of the medical device.

BRIEF DESCRIPTION OF THE DRAWINGS

By means of drawings, the invention will be explained in more detail in the following on the basis of embodiments, in which.

EMBODIMENTS

Additional advantages, characteristics and features of the present invention will become clear in the following detailed description of embodiments and on the basis of the attached drawings. However, the invention is not restricted to these embodiments.

Before discussing the drawings in any more detail, it should firstly be noted that the same or corresponding means or elements are denoted by the same reference signs in all the drawings.

Figure 1:
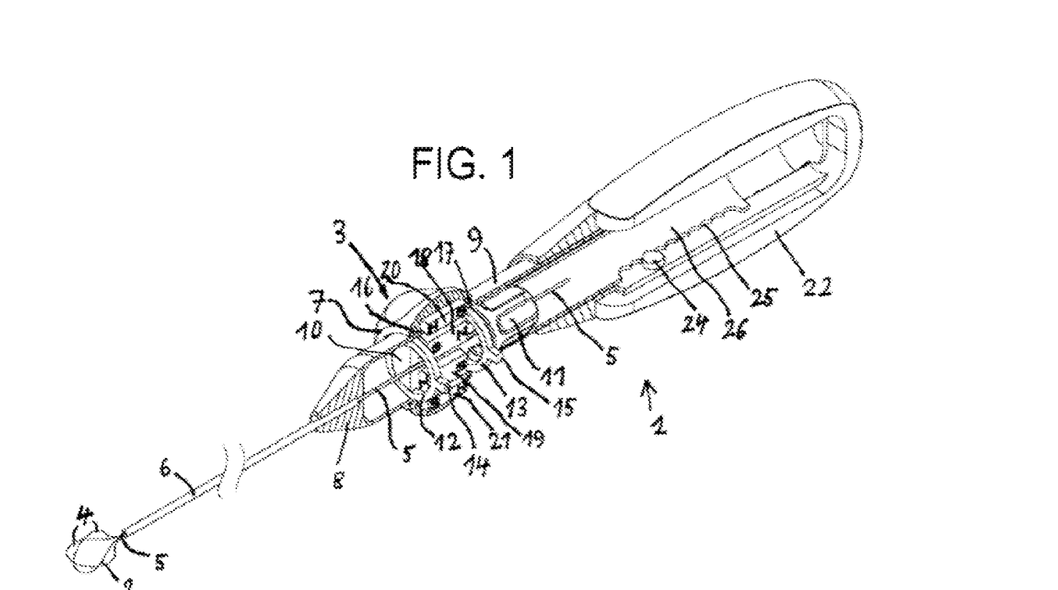
FIG. 1 is a perspective view of a medical device according to one embodiment of the invention in a size that may differ from the size used in practice.

FIG. 1 is a perspective view of a medical device 1 according to one embodiment of the invention in a size that may differ from the size used in practice. The medical device 1 contains a medical instrument 2, which is shown as a stone retrieval basket 2 here, for example for catching gallstones or kidney stones. This medical instrument 2 can be moved by an actuating means 3 of the medical device 1 in the device longitudinal direction and in the direction of rotation that is transverse about the particular longitudinal direction by means of a single-handed movement. In this case, the actuating means 3 comprises a rotary slide 7, as will become even more apparent.

The above-mentioned stone retrieval basket 2 consists of basket strands 4, which, together with a pulling and sliding strand 5, are received by an outer tube 6, in which outer tube this pulling and sliding strand can be moved in its longitudinal direction. By moving the pulling and sliding strand 5 in the direction towards the distal (shown on the left in FIG. 1) device end, the basket strands 4 can be pushed out of the outer tube 6 and the stone retrieval basket 2 can be opened; by moving the pulling and sliding strand 5 towards the opposite proximal (shown on the right in FIG. 1) device end or by retracting the pulling and sliding strand 5 into the outer tube 6, the basket strands 4 comprising the pulling and sliding strand 5 can close again and thereby receive stone concretions, for example, in the stone retrieval basket 2 and hold them by means of said basket.

The medical device 1 contains a distal device tip part 8, to which a cover tube 9 connects towards the proximal device end, which tube can be formed as an extension part of the device tip part 8.

As is clear from FIG. 1, the outer tube 6 of the medical instrument 2 is fixedly received by the device tip part 8. The pulling and sliding strand 5 that is guided inside this outer tube 6 extends inside the cover tube 9 mentioned where it is tightly received by a receiving body 10, which is surrounded by the rotary slide 7 already mentioned above and forms the actuating means 3 together therewith. This set-up is shown very generally in FIGS. 2 and 3, which show the medical device 1 according to FIG. 1 having a slightly modified design at the proximal device end.

Figure 3:
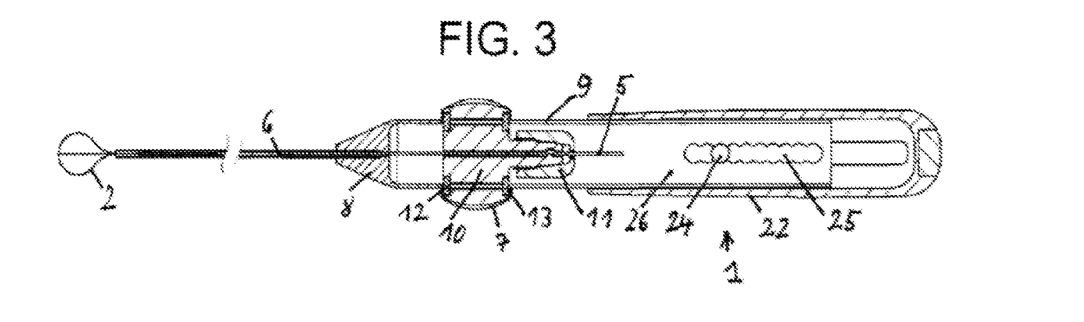
FIG. 3 is a sectional view of the embodiment shown in FIG. 2 of the medical device according to the invention.

The pulling and sliding strand 5 is—as is clear from the sectional view according to FIG. 3—secured in the receiving body 10 by a clamping part 11 that is screwed thereon such that it cannot be pulled out of or pushed into the particular receiving body 10. Annular elements 12, 13 are connected to the receiving body 10 at the distal and proximal ends thereof, which annular elements are provided with protruding pins 14 and 15 (shown in FIG. 1), which are received by a slot (not shown) in the cover tube 9 for guidance purposes. In this case, the two pins 12, 13 slightly protrude beyond the outer circumference of the cover tube 9 by their ends. Those parts of the pins 14, 15 that protrude beyond the outer circumference of the cover tube 9 are received by circumferential grooves 16 and 17 in the internal circumference of the rotary slide 7. By means of this mechanical coupling, the rotary slide 7 can be rotated transversely to the device longitudinal direction relative to the receiving body 10 and can be moved in the device longitudinal direction together with the receiving body 10.

In order to transform the above-mentioned rotary motion of the rotary slide into a rotary motion of the pulling and sliding strand 5 and therefore into a corresponding rotary motion of the medical stone retrieval basket 2, according to the invention, the receiving body 10 that holds the pulling and sliding strand 5 in position is provided with at least one first magnetic element—which has two diametrically opposing first magnetic elements 18, 19 according to FIG. 1. In this case, these magnetic elements 18, 19 are formed by individual bar-shaped permanent magnets, which are fixedly attached to the receiving body 10, for example by means of adhesion. The orientation of the magnetic poles—north pole (N) and south pole (S)—extends in the device longitudinal direction in this case.

The at least one first magnetic element having two permanent magnets 18, 19 that are opposite one another with a small spacing therebetween and fixedly attached to the receiving body 10 is arranged near to at least one second magnetic element which is formed by two corresponding bar-shaped permanent magnets 20 and 21 which in this case are attached to the inside of the rotary slide 7, likewise by means of adhesion, for example. The orientation of the magnetic poles north pole (N) and south pole (S)—of the permanent magnets 20, 21 extends in the device longitudinal direction in this case—contrary to the orientation of the magnetic poles—north pole (N) and south pole (S)—of the permanent magnets 18 and 19. As a result, the permanent magnets 18 and 20 and the permanent magnets 19 and 21 attract one another in each case. It should be noted here that the permanent magnets 18 and 20 and 19 and 21 could also be oriented so that their magnetic poles are the same, such that the north pole (N) and the south pole (S) are opposite one another in each case. In this case, according to FIG. 1, the rotary motion of the medical device or the stone retrieval basket 2 as a result of the rotational movement of the rotary slide 7 is therefore brought about by the magnetic coupling between the permanent magnets 18 and 20 and 19 and 21 during the longitudinal movement of the medical device or the stone retrieval basket 2 as a result of the mechanical coupling between the rotary slide 7 and the receiving body 10 mentioned.

An end gripping part 22, which is bulge-shaped and can be attached to the cover tube 9 such that it can move is connected to the cover tube 9 at the proximal (shown on the right in FIG. 1) device end. In this case, this end gripping part 22 carries a latching roller 24 in its interior, which is able to sit in latching openings 25 of a latching element strip 26, which strip is formed as part of the cover tube 9 in this case.

Figure 2:
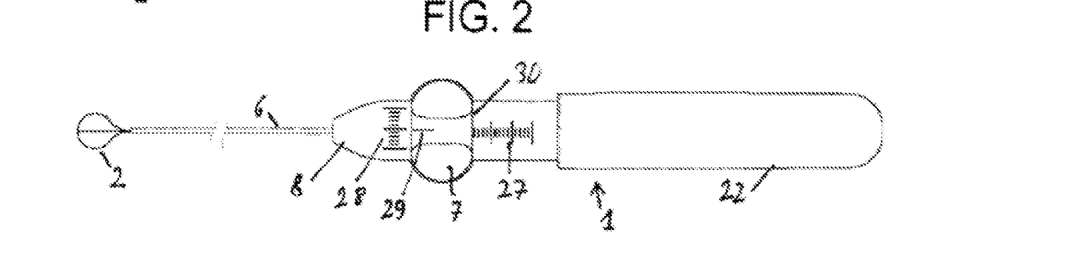
FIG. 2 is a plan view of the medical device according to FIG. 1 in a slightly modified embodiment and in a size that may likewise differ from the size used in practice.

FIG. 2 shows that the medical device 1 is provided with a scale means, which consists of two scales 27 and 28 in this case, which have graduations in millimeters/inches or angular degrees, for example, and can additionally be provided with measurements. The scale 27 for specifying the length is provided on the outside of the cover tube 9; when measuring how far the medical instrument or stone retrieval basket extends out of the medical device 1, in this case the outer edge 30 of the rotary slide 7 shown on the right in FIG. 2 can be used as the reference element. By means of the scale 28 attached to the distal device tip part 4, which is used to measure angular degrees, the rotation of the rotary slide 7 and therefore of the medical instrument or stone retrieval basket can be measured. For this measurement, a pointer 29 that is attached to the outside of the rotary slide 7 near to the scale is assigned to the scale 28.

The sectional view shown in FIG. 3 of the medical device 1 shown in FIG. 2 indicates that, in this case, unlike the embodiment shown in FIG. 1, the end gripping part 22 is cylindrical. As in FIG. 1, the latching element strip 26 comprising the latching openings 25 and the latching roller 24 is also provided here.

Figure 4:
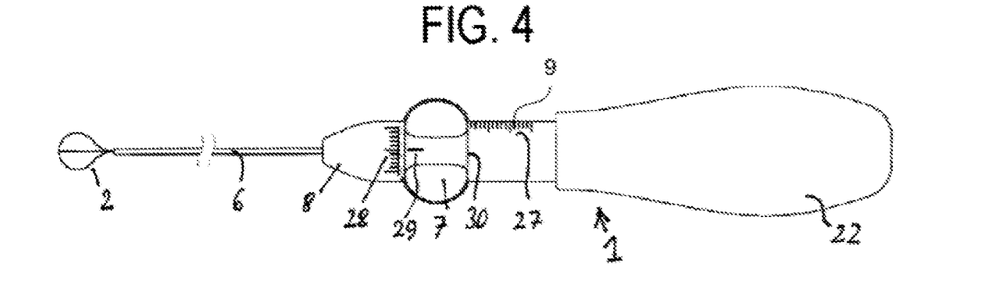
FIG. 4 is a plan view of a medical device according to another embodiment of the invention, likewise in a size that may differ from the size used in practice.
Figure 5:
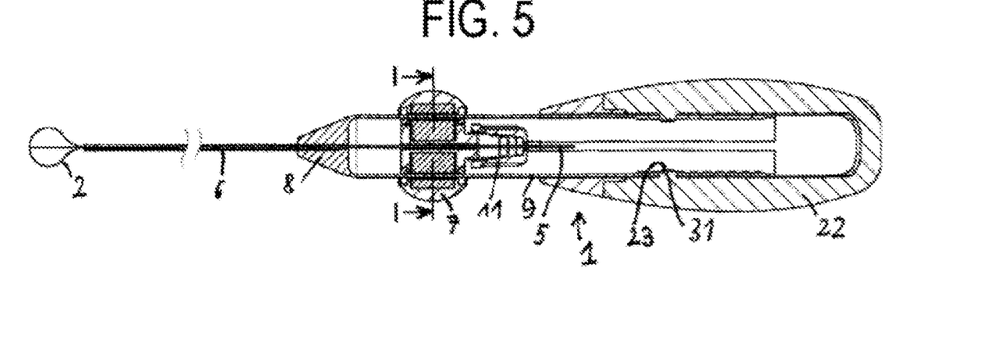
FIG. 5 is a sectional view of the embodiment shown in FIG. 4 of the medical device according to the invention.

FIGS. 4 and 5 are a plan view and a sectional view, respectively, of a medical device 1 according to another embodiment of the invention. In this case, the bulge-shaped end gripping part 22 is held in position on the cover tube 9 by a latching connection, which consists of a latching lug 31 on the end gripping part 22 and a matching locking opening 23 in the cover tube 9.

Figure 6:
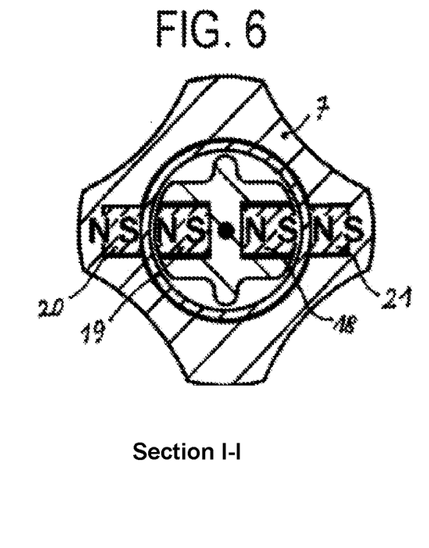
FIG. 6 is an enlarged sectional view according to the sectional line I-I drawn in FIG. 5.
Figure 7:
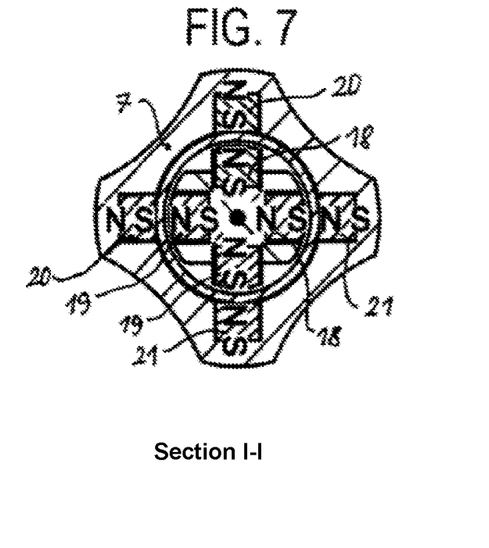
FIG. 7 is another enlarged sectional view according to the sectional line I-I drawn in FIG. 5.
Figure 8:
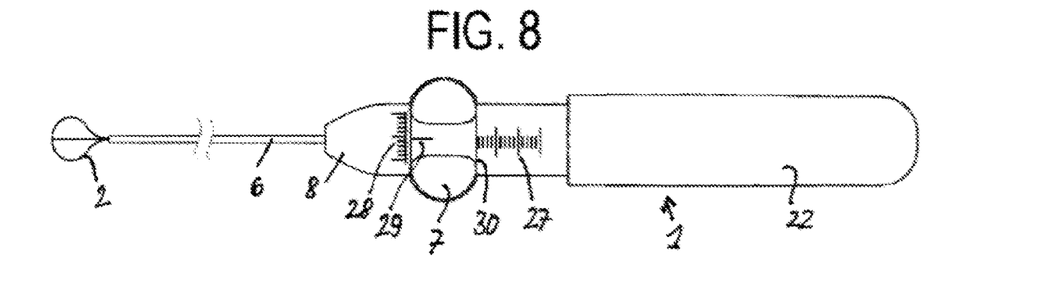
FIG. 8 is a plan view of a medical device according to another embodiment of the invention, likewise in a size that may differ from the size used in practice.
Figure 9:
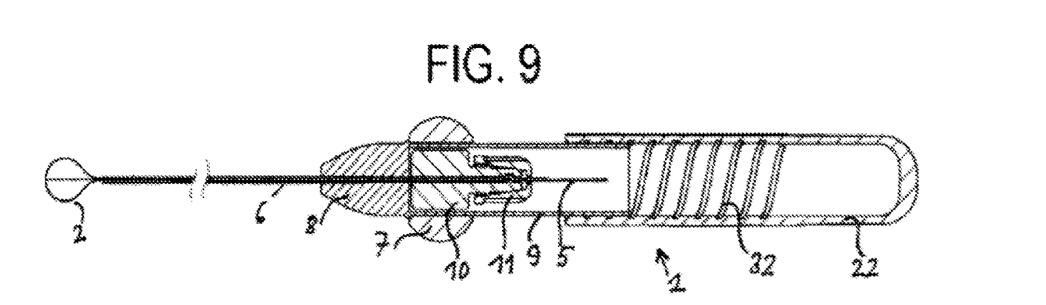
FIG. 9 is a sectional view of the embodiment shown in FIG. 8 of the medical device according to the invention.
Figure 10:
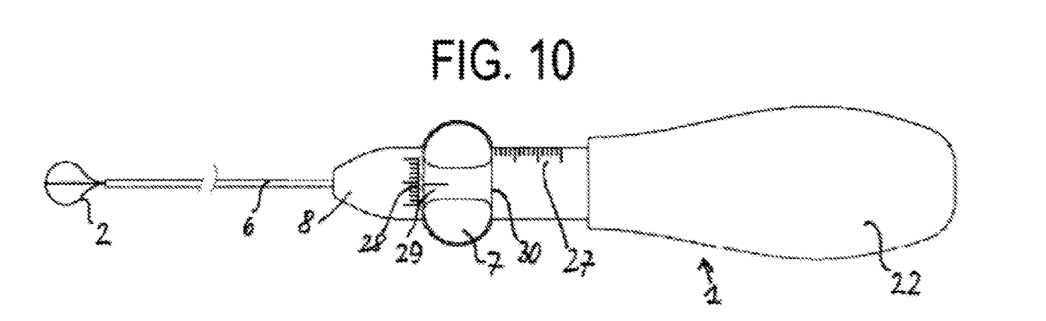
FIG. 10 is a plan view of a medical device according to another embodiment of the invention, likewise in a size that may differ from the size used in practice.

FIGS. 6 and 7 are enlarged sectional views along the section line I-I drawn in FIG. 5. In this case, FIG. 6 shows a first magnetic element 18, 19 and second magnetic element 20, 21, each in the form of a bar-shaped permanent magnet on diametrically opposing sides of the receiving body 10 or the rotary slide 7. In this case, the poles of the permanent magnets 18, 21 and 19, 20 are oriented such that the opposite poles thereof (north pole N and south pole S) are opposite one another and therefore attract the particular permanent magnets. FIG. 7 shows a crossed arrangement of two sets of permanent magnets 18 to 21, which are offset with respect to one another by 90° C. and have corresponding polarity (N and S).

It should be noted here that the permanent magnets 18, 21 and 19, 20 mentioned can in principle also be polarized differently to that shown in FIGS. 6 and 7, i.e. can each be arranged with the same poles (either N poles or S poles) opposite one another.

FIGS. 8, 9, 10 and 11 show additional modifications of embodiments of the medical device 1 according to the invention. These modifications substantially differ from the previously considered embodiments of the medical device 1 according to the invention in that the particular end gripping part 22 is screwed onto the cover tube 9 by means of a screw thread 32. As a result, a length that is comfortable for the particular user and a desired opening length for the stone retrieval basket 2 can be set in a simple manner by means of the proximal device region that can be used as a hand rest when operating the device single-handedly.

Figure 11:
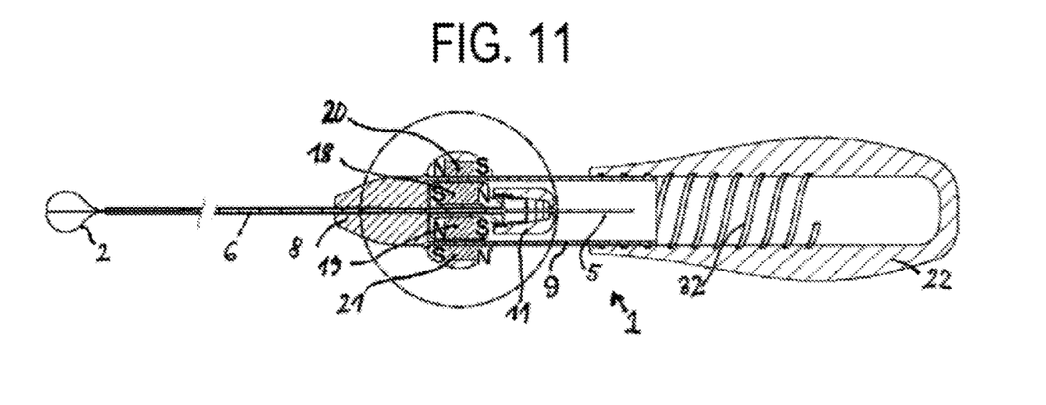
FIG. 11 is a sectional view of the embodiment shown in FIG. 10 of the medical device according to the invention.

FIGS. 12, 13, 14 and 15 are enlarged cut-outs of a region that is surrounded by a dash-dot circle in FIG. 11—this is the actuating region 3 of the medical device 1 that comprises the rotary slide 7 and the receiving body 10.

Figure 12:
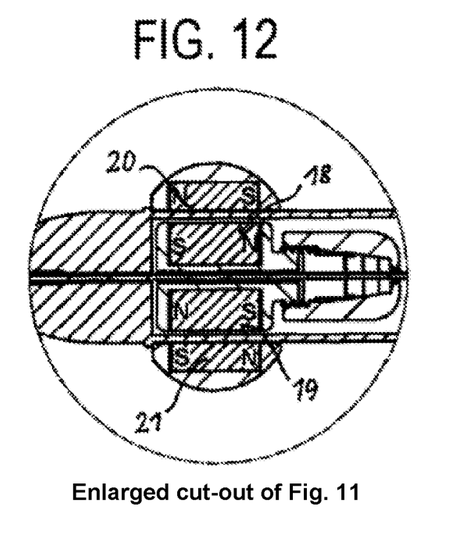
FIG. 12 is an enlarged cut-out of FIG. 11.
Figure 13:
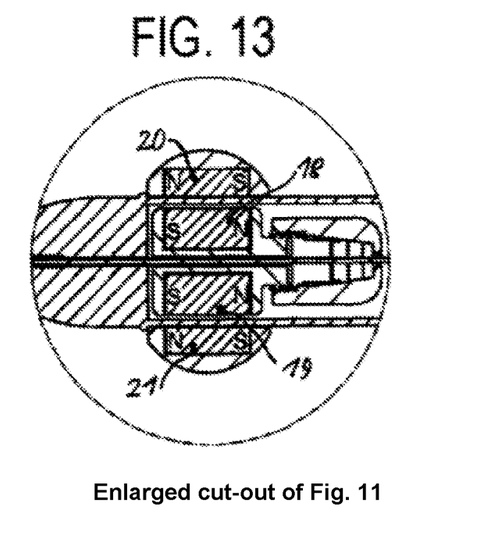
FIG. 13 is another enlarged cut-out of FIG. 11.

In this case, FIGS. 12 and 13 show the use of bar-shaped permanent magnets 18, 19, 20 and 21, the polarity of which (north pole N and south pole S) is oriented in the longitudinal direction of the medical device 1 in each case. In FIG. 12, the opposite permanent magnets 18, 20 and 19, 21 attract one another by means of their opposite poles (N-S). In contrast, in FIG. 13, the opposite permanent magnets 18, 20 and 19, 21 repel one another by means of their opposite poles (N-S).

Figure 14:
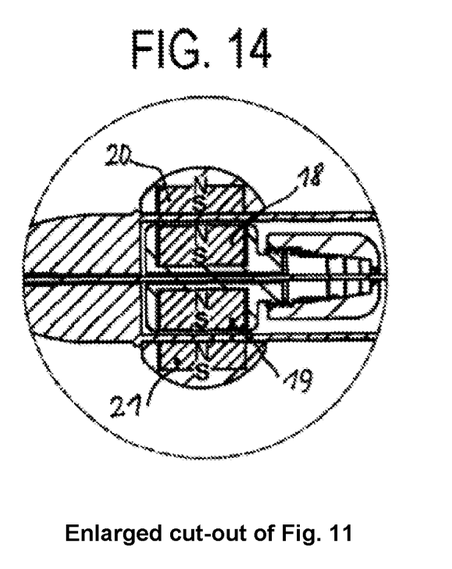
FIG. 14 is yet another enlarged cut-out of FIG. 11.
Figure 15:
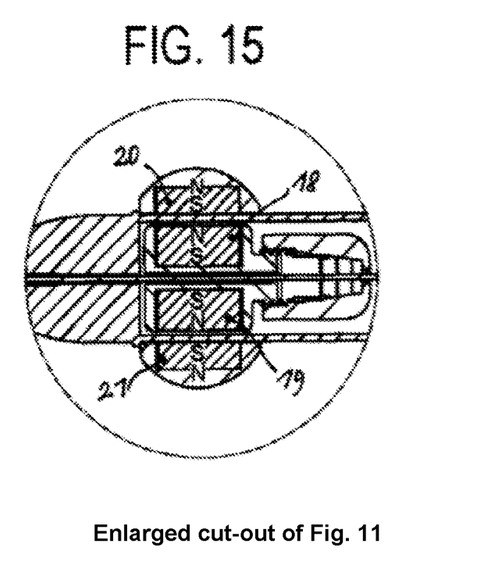
FIG. 15 is an additional enlarged cut-out of FIG. 11.

FIG. 14 and FIG. 15 show the circumstances for permanent circular magnets 18 to 21, which correspond to the circumstances shown in FIG. 12 and FIG. 13 with respect to the permanent magnets 18 to 21, the opposite poles of which permanent circular magnets (north-south) are each oriented transversely to the device longitudinal direction. In this case, FIG. 14 shows that the opposite permanent circular magnets 18, 20 and 19, 21 attract one another by means of their opposite poles (N-S). In contrast, in FIG. 15, the opposite permanent circular magnets 18, 20 and 19, 21 repel one another by means of their opposite poles (N-S).

Finally, it should be noted that the invention can also be implemented using other medical instruments 2 to the stone retrieval basket described. Therefore, forceps, such as endoscopically usable forceps, snares, such as polypectomy snares, or medical or surgical handling tools can be used as the medical instruments.

The at least one magnetic elements 18, 19, 20, 21 have previously been described as each containing two or four magnetic elements. However, it should be noted that a larger number of the particular magnetic elements can also be provided, specifically preferably always a first magnetic element and a second magnetic element in a pair. In this case, as already mentioned at the outset, some, a plurality of or all the particular magnetic elements can be formed by electromagnetic elements.

FIGS. 16 to 21 show the same embodiment of a medical device 1 according to the invention, in which the actuating means 3 comprises a rotary slide 7 and a scale element 33 having an L-shaped cross section. In addition, several of the elements of the embodiment shown here are similar to those in the embodiment shown in FIGS. 10 and 11. The elements already described for those figures are therefore not intended to be described in detail again here.

It can be seen that both the rotary slide 7 and the end gripping part 22 comprise grooves, which allow the elements to be held and operated particularly securely.

In FIGS. 16 to 21, the first magnetic elements 18, 19 are each oriented by means of magnetic interaction at their opposite poles in the second magnetic elements 20, 21.

Figure 17:
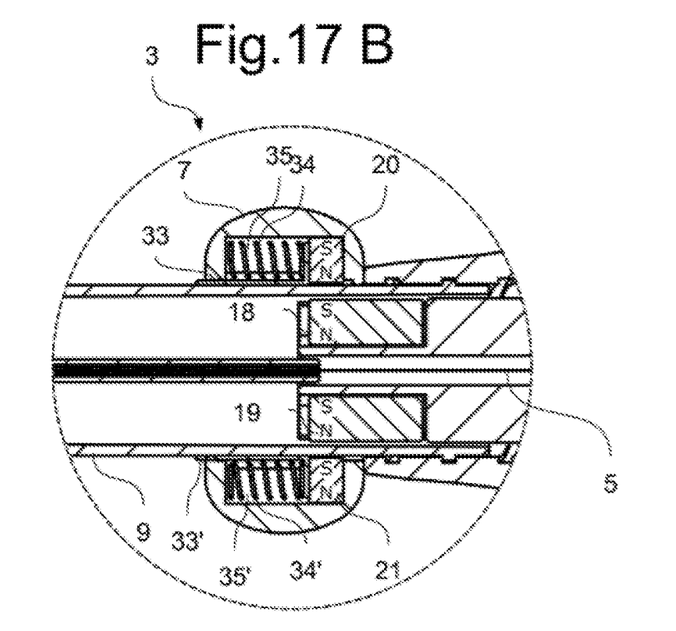
FIG. 17 is a sectional view of a proximal part of the embodiment shown in FIG. 16 of the medical device according to the invention (A) and an enlarged sectional view of the rotary slide shown in FIG. 17A (B)
Figure 17A:
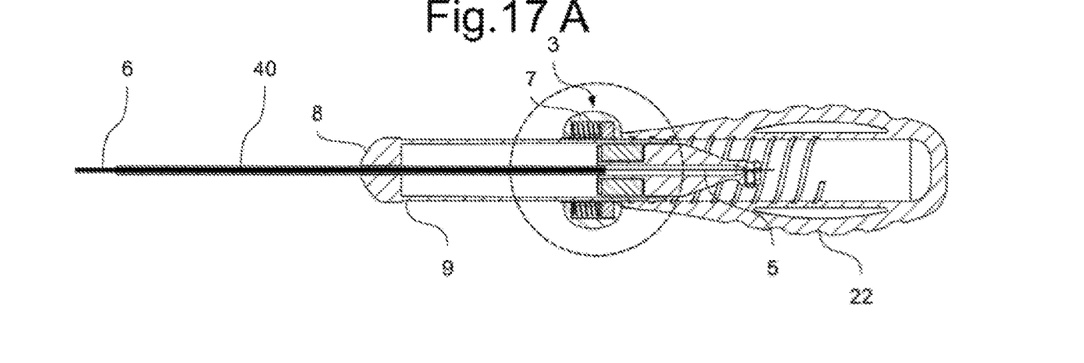

In the sectional views in FIGS. 17A and B, it can be seen that the rotary slide 7 of the medical device 1 comprises two cavities 35, 35'. The cavities 35, 35' are radially open towards the cover tube 9. They extend lengthwise in parallel with the longitudinal axis of the medical device 1 and therefore also in parallel with the cover tube 9. A spring element 34 and 34', a second magnetic element 20 and 21 and part of a scale element 33 and 33', are arranged inside the cavities 35, 35', respectively. In this case, the spring element 34 and 34' is arranged distally from the part of a scale element 33 and 33' and the part of a scale element 33 and 33' is arranged distally from the second magnetic element 20 and 21, respectively. The length of the cavities 35, 35' preferably corresponds to the combined length of the second magnetic element 20 and 21, the spring element 34 and 34' and the part of the scale element 33 and 33', respectively, in each case, wherein the spring element 34 and 34' is not fully compressed. Whilst the spring element 34 and 34' does not have to be completely relaxed in this position, it is preferable for the spring elements 34, 34' to be almost or completely relaxed in this non-operative position, i.e. substantially completely relaxed. This ensures that the spring elements 34, 34' can be compressed in the distal direction.

Figure 16:
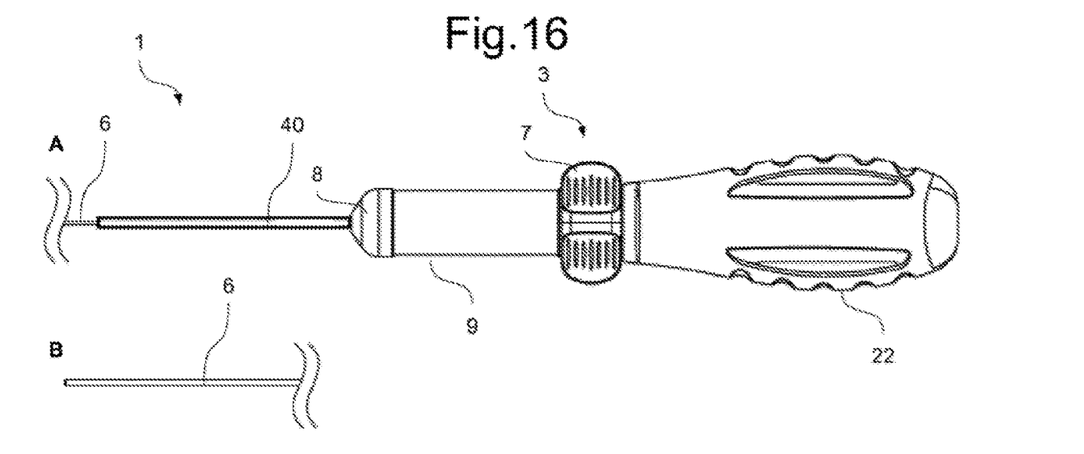
FIG. 16 is a plan view of a medical device according to another embodiment of the invention, which comprises a scale element, which is visible in FIG. 17B, has an L-shaped cross section and by means of which the length of a concretion received in the stone retrieval basket can be measured, and wherein the medical instrument is completely drawn back into the outer tube (A: proximal portion; B: distal end region)
Figure 20:
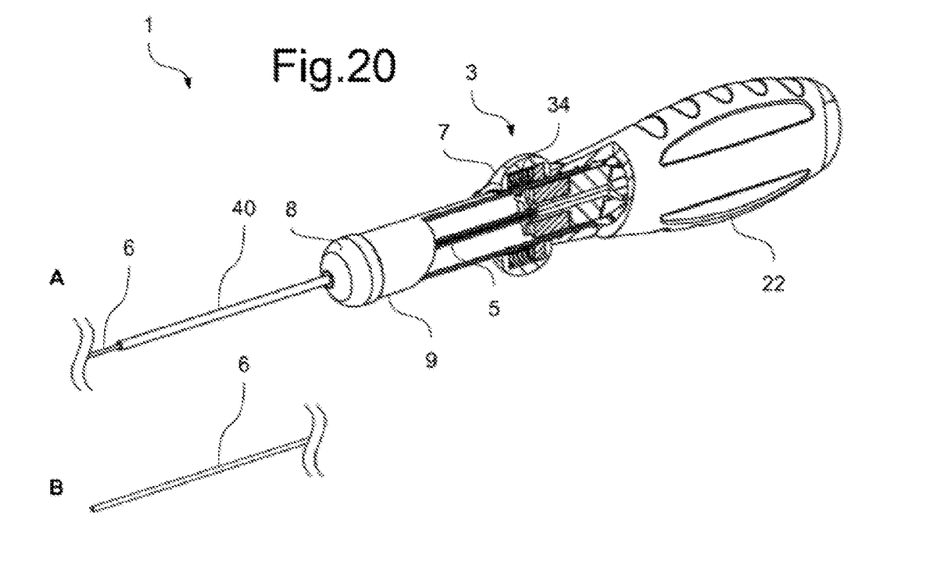
FIG. 20 is a perspective view of a medical device according to the embodiment and position shown in FIGS. 16 and 17, wherein the medical instrument is completely drawn back into the outer tube (A: proximal portion; B: distal end region)

In the position shown in FIGS. 16, 17 and 20, the medical instrument 2 is fully drawn back into the outer tube 6 of the medical device 1 in the proximal direction. This position is also referred to as the "non-operative position" here. It is only possible for the medical instrument 2 to be fully drawn back into the outer tube 6 when a concretion 42 is not received between the basket strands 4. In this position, the medical device 1 can be inserted into an opening in the patient's body, for example, and brought to the surgical site.

In order to prevent the outer tube 6 from kinking behind the device tip part 8, the medical device 1 in FIGS. 16 to 23 comprises an anti-kink tube 40, which is wrapped around the outer tube 6 immediately distally from the device tip part 8 and stabilizes it. The anti-kink tube 40 is a hose-shaped flexible element, in the interior of which the outer tube 40 extends. The anti-kink tube 40 is considerably shorter than the outer tube 40.

It can be seen in FIGS. 17 and 20 that the spring elements 34, 34' are substantially relaxed and exert a spring force on the second part of the scale element 33, 33' in the proximal direction. The scale element 33 and 33' comprises an L-shaped cross section and is therefore made up of a first part, which extends in parallel with the longitudinal axis of the medical device 1, and a second part, which, starting from the proximal end of the first part, extends orthogonally from the cover tube 9 and radially into the cavity 35 and 35', respectively. In the embodiment shown, the scale element 33, 33' is made of one piece, wherein a 90° angle is formed between the first and the second part of the scale element 33, 33'. The spring force of the spring element 34, 34' pushes the second part of the scale element 33, 33' against the second magnetic element 20 and 21, respectively.

Figure 18:
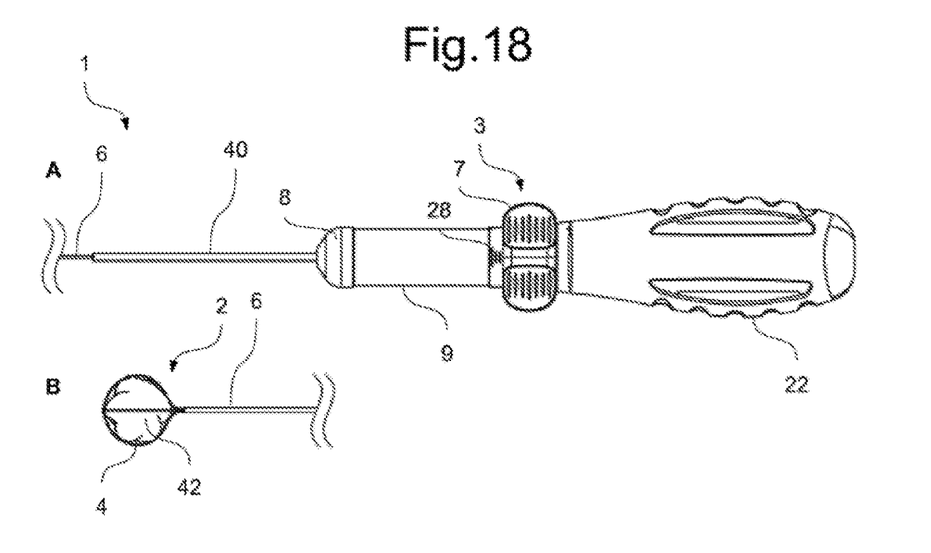
FIG. 18 is a plan view of the embodiment shown in FIG. 16-17, wherein a concretion is received in the distal stone retrieval basket (A: proximal portion; B: distal end region)
Figure 19:
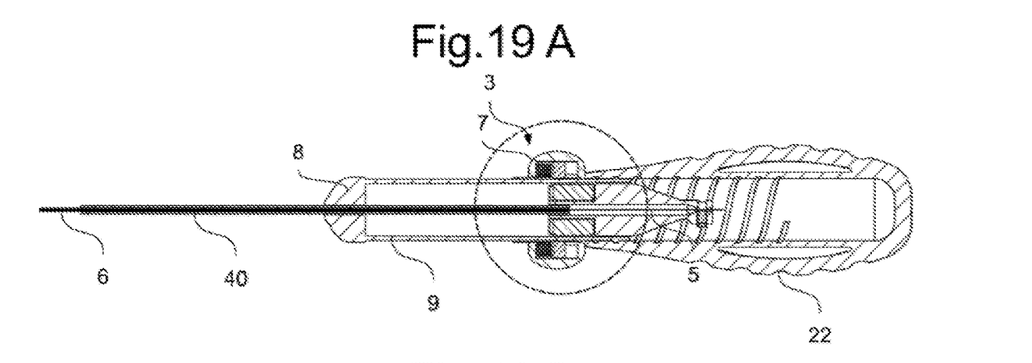
FIG. 19 is a sectional view of a proximal part of the embodiment shown in FIG. 16-18, wherein a concretion is received in the distal stone retrieval basket in a manner that is not shown (A), and an enlarged sectional view of the rotary slide shown in FIG. 19A (B)
Figure 21:
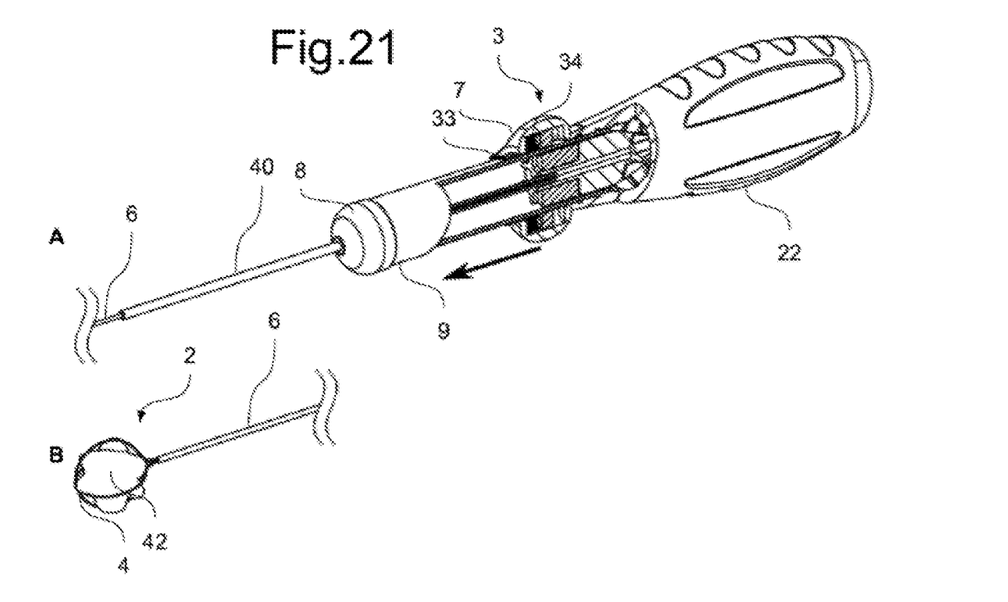
FIG. 21 is a perspective view of a medical device according to the embodiment and position shown in FIGS. 18 and 19, wherein a concretion is received in the distal stone retrieval basket (A: proximal portion; B: distal end region)

FIGS. 18, 19 and 21 show a position in which the stone retrieval basket 2 is distally pushed out of the outer tube 6 and has received a concretion 42, for example a kidney stone, between the basket strands 4. The pulling and sliding strand 5 is drawn back into the outer tube 6 as far as possible in this case, i.e. to such an extent that the basket strands 4 have wound tightly around the concretion 42 over substantially their entire length. After this position has been reached, the rotary slide 7 was moved further in the proximal direction so that, by means of the magnetic interaction between the first and second magnetic elements 18, 19, 20, 21 and with the compression of the spring element 34, 34', the second part of the scale element 33, 33' was moved in the distal direction. By means of the movement of the scale element 33, 33' in the distal direction, the distal portion of the first part of the scale element 33, 33' is pushed forwards between the rotary slide 7 and the cover tube 9 so that the scale arranged on the scale element 33, 33' can be read off by the user of the element.

Figure 22:
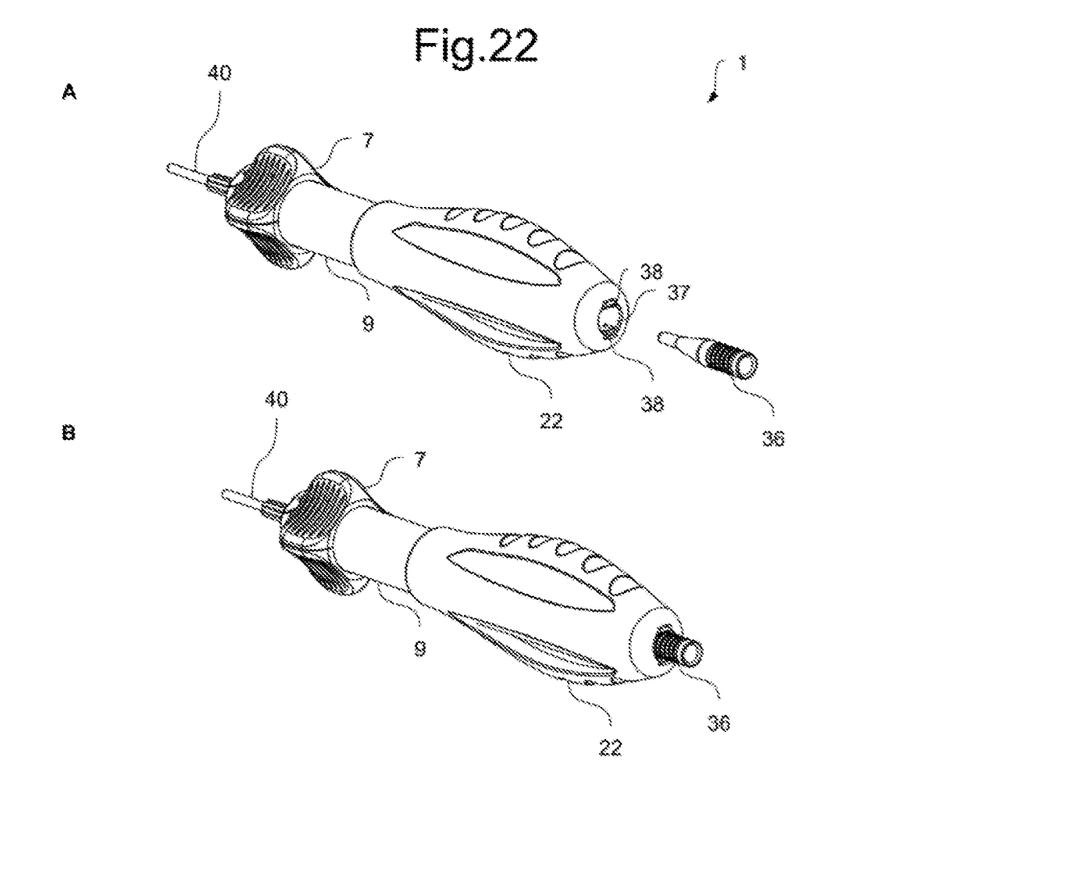
FIG. 22 is a perspective view of a proximal part of a medical device according to another embodiment, at the proximal end of which a fixing aid is arranged, wherein, in (A), the fixing aid is removed from the end gripping part and, in (B), is introduced into the end gripping part.
Figure 23:
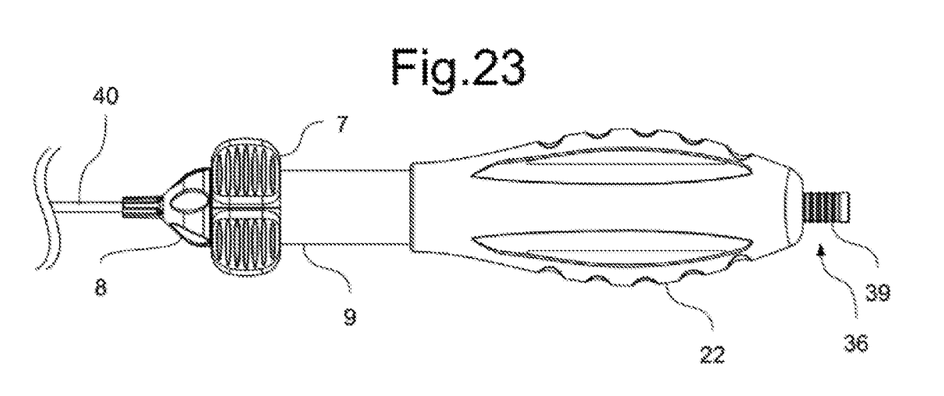
FIG. 23 is a lateral plan view of the embodiment shown in FIG. 22 of the medical device according to the invention.

FIGS. 22 and 23 show perspective views, FIGS. 22A and B, and a lateral view, FIG. 23, of a medical device 1 according to another embodiment according to the invention, at the proximal end of which an insertion aid 36 is arranged. The medical device 1 comprises an outer tube 6 distally from the end gripping part 22, in which tube the pulling and sliding strand 5 (not shown here) extends. The end gripping part 22 comprises a rotary slide 7 of the type according to the invention, which surrounds a cover tube 9 that continues proximally from the rotary slide 7 in the end gripping part 22.

At its proximal end, the medical device 22 comprises an opening 37, into which an insertion aid 36 can be inserted. As can be seen in FIG. 23, the insertion aid 36 comprises a cylindrical proximal region, on the outer circumference of which circumferential ribs 39 are arranged. When inserting the insertion aid 36 into the opening 37, the shape and size of which complement that of the aid, clamping elements 38 arranged on the opening 37 engage in the gaps between the ribs 39 and slide over the ribs 39. The insertion aid 36, as can be seen in FIG. 22, comprises a short cylindrical distal portion and a portion arranged proximally thereto, which cylindrically distally converge. In FIG. 22, part A depicts a position in which the insertion aid 36 is removed from the end gripping part 22, and part B shows a position in which the insertion aid 36 is locked in the end gripping part 22.

Even though the present invention has been described in detail on the basis of the embodiments, it is self-evident to a person skilled in the art that the invention is not restricted to these embodiments, but instead modifications are possible whereby individual features can be left out or different combinations of the individual features presented can be implemented, provided that the scope of protection of the attached claims is not left. The present disclosure includes all combinations of the individual features presented.

LIST OF REFERENCE NUMERALS 1 medical device
2 medical instrument, stone retrieval basket
3 actuating means
4 basket strand
5 pulling and sliding strand
6 outer tube
7 rotary slide
8 device tip part
9 cover tube
10 instrument receiving body, receiving body
11 clamping part
12 annular element
13 annular element
14 pin
15 pin
16 groove
17 groove
18 first magnetic element, permanent magnet
19 first magnetic element, permanent magnet
20 second magnetic element, permanent magnet
21 second magnetic element, permanent magnet
22 end gripping part
23 locking opening
24 latching roller
25 latching openings
26 latching element strip
27 scale
28 scale
29 pointer
30 outer edge
31 latching lug
32 screw thread
33, 33' scale element
34, 34' spring element
35, 35' cavity
36 insertion aid
37 proximal opening
38 clamping element
39 rib
40 anti-kink tube
42 concretion

The invention claimed is:

1. A medical device comprising:
a medical instrument; and
an actuating means for moving the medical instrument by single-hand operation both in a longitudinal direction of the device and in a direction of rotation that is transverse to the longitudinal direction of the device;
wherein the medical instrument contains at least one first magnetic element or at least one first magnetic element is connected to the medical instrument,
wherein the actuating means contains at least one second magnetic element or at least one second magnetic element is connected to the actuating means,
wherein the at least one second magnetic element is received by a rotary slide of the actuating means, which, together with the at least one second magnetic element is movable around the at least one first magnetic element in both the longitudinal direction and in the direction of rotation,
wherein the actuating means is either:
(a) mechanically coupled to the at least one second magnetic element and only allows the at least one first magnetic element to move in the direction of rotation as a result of magnetic coupling, or,
(b) is not mechanically coupled to the at least one second magnetic element and allows the at least one first magnetic element to move in both the longitudinal direction and the direction of rotation as a result of magnetic coupling, and
wherein the medical device comprises a scale element and by means of longitudinal movement of the at least one second magnetic element in a distal direction, the scale element is movable in the distal direction.

2. The medical device according to claim 1, wherein part of the scale element is spring-preloaded in a proximal direction and is arranged in a cavity distally from the at least one second magnetic element.

3. A medical device comprising:
a medical instrument connected to a pulling and sliding strand;
an outer tube through which the pulling and sliding strand passes;
a device handle having a gripping part, a cover tube and a tip part; and
a rotary slide that surrounds the cover tube;
wherein the outer tube is fixed within the tip part,
wherein the pulling and sliding strand is held by a receiving body that is movably received within the cover tube,
wherein the receiving body comprises at least one first magnetic element,
wherein the rotary slide comprises at least one second magnetic element, and
wherein the rotary slide is available at all times to move the medical instrument by single-hand operation in a longitudinal direction of the device and in a direction that is rotationally transverse to the longitudinal direction of the device as a result of magnetic coupling between the at least one first magnetic element and the at least one second magnetic element.

4. The medical device according to claim 3, wherein a scale means is provided on the cover tube and/or on the tip part handle for determining or indicating an amount of movement of the medical instrument in the longitudinal direction of the device and/or in the direction that is rotationally transverse to the longitudinal direction of the device.

5. The medical device according to claim 3, wherein the at least one first magnetic element and the at least one second magnetic element are arranged such that they interact with opposite magnetic poles, namely north pole N and south pole S.

6. The medical device according to claim 3, wherein the at least one first magnetic element and the at least one second magnetic element are bar magnets, the opposite poles of which, namely north pole N and south pole S, are each oriented in the longitudinal direction of the device.

7. The medical device according to claim 3, wherein the at least one first magnetic element and the at least one second magnetic element are circular magnets, the opposite poles of which, namely north pole N and south pole S, are each oriented transversely to the longitudinal direction of the device.

8. The medical device according to claim 3, wherein the at least one first magnetic element and the at least one second magnetic element are permanent magnets.

9. The medical device according to claim 3, wherein the medical instrument is an endoscopically usable medical instrument, a medical stone retrieval basket or a medical snare.

10. The medical device according to claim 3, wherein the rotary slide has at least one cavity in which the at least one second magnetic element is arranged such that the at least one second magnetic element is movable in the longitudinal direction of the device.

11. The medical device according to claim 3, wherein the receiving body comprises a plurality of first magnetic elements, and wherein the rotary slide comprises a plurality of second magnetic elements.

* * * * *